United States Patent [19]
Sondhi et al.

[11] Patent Number: 5,971,754
[45] Date of Patent: Oct. 26, 1999

[54] INDIRECT BONDING METHOD AND ADHESIVE FOR ORTHODONTIC TREATMENT

[76] Inventors: Anoop Sondhi; Darrell S. James; Jerold S. Horn, all of P.O. Box 33427, St. Paul, Minn. 55133-3427

[21] Appl. No.: 09/126,069

[22] Filed: Jul. 30, 1998

[51] Int. Cl.⁶ .................................................. A61C 3/00
[52] U.S. Cl. .................................. 433/24; 433/8; 526/278
[58] Field of Search .............................. 433/24, 8, 9, 16, 433/17, 20; 526/278, 276, 277; 106/35

[56] References Cited

U.S. PATENT DOCUMENTS

| | | | |
|---|---|---|---|
| 3,949,477 | 4/1976 | Cohen et al. | 32/14 A |
| 4,499,251 | 2/1985 | Omura et al. | 526/278 |
| 4,501,554 | 2/1985 | Hickham | 433/24 |
| 4,503,169 | 3/1985 | Randklev | 523/117 |
| 4,515,930 | 5/1985 | Omura et al. | 526/276 |
| 4,537,940 | 8/1985 | Omura et al. | 526/278 |
| 4,539,382 | 9/1985 | Omura et al. | 526/276 |
| 4,695,251 | 9/1987 | Randklev | 433/8 |
| 5,015,180 | 5/1991 | Randklev | 433/9 |
| 5,110,290 | 5/1992 | Wong | 433/9 |
| 5,154,762 | 10/1992 | Mitra et al. | 106/35 |
| 5,172,809 | 12/1992 | Jacobs et al. | 206/368 |
| 5,328,363 | 7/1994 | Chester et al. | 433/9 |
| 5,354,199 | 10/1994 | Jacobs et al. | 433/9 |
| 5,429,229 | 7/1995 | Chester et al. | 206/63.5 |
| 5,474,448 | 12/1995 | Andreiko et al. | 433/24 |
| 5,518,397 | 5/1996 | Andreiko et al. | 433/24 |
| 5,533,895 | 7/1996 | Andreiko et al. | 433/24 |
| 5,575,645 | 11/1996 | Jacobs et al. | 433/9 |

OTHER PUBLICATIONS

Thomas, Royce G., "Indirect Bonding/Simplicity in Action", Journal of Clinical Orthodontics, vol. XIII, #2, pp. 93–95. Feb. 1979.

Thomas, Royce G., "Indirect Bonding/Simplicity in Action", *Journal of Clinical Orthodontics*, vol. XIII, No. 2, pp. 93–105. Feb. 1979.

Read and O'Brien, "A clinical trial of an indirect bonding technique with a visible light–cured adhesive", *American Journal of Orthodontics and Dentofacial Orthopedics*, Sep. 1990, vol. 98, No. 3, pp. 259–262.

Moskowitz, Knight, Sheridan, Esmay and Tovilo, "A New Look at Indirect Bonding", *Journal of Clinical Orthodontics*, vol. XXX No. 5, pp. 277–281. Jun. 1997.

Kasrovi, Timmins and Shen, "A new approach to indirect bonding using light–cure composites", *American Journal of Orthodontics and Dentofacial Orthopedics*, Jun. 1997, vol. 111 No. 6, pp. 652–656.

*Primary Examiner*—Gene Mancene
*Assistant Examiner*—Pedro Philogene
*Attorney, Agent, or Firm*—James D. Christoff

[57] ABSTRACT

A method of indirect bonding used in orthodontic treatment includes the steps of placing a first component of an adhesive on base structure of an orthodontic appliance and a second component of the adhesive on portions of a patient's tooth. The appliance is connected to a transfer tray, and the transfer tray is placed over the tooth such that the first component and the second component contact each other and react to provide a bond for securing the appliance to the tooth. The bond has sufficient strength within two minutes and preferably within 1.5 minutes of the time that the first component contacts the second component to enable removal of the tray from the tooth without significantly changing the position of the appliance on the tooth.

20 Claims, 2 Drawing Sheets

INDIRECT BONDING METHOD AND ADHESIVE FOR ORTHODONTIC TREATMENT

BACKGROUND OF THE INVENTION

1. Field of the Invention

This invention relates to a method and adhesive for bonding orthodontic appliances such as brackets to a patient's teeth. More specifically, the present invention relates to an indirect bonding method wherein the ultimate position of the appliance on the teeth is determined in part by use of a stone model and transfer tray, and wherein the adhesive provides specific advantages for carrying out the method.

2. Description of the Related Art

Orthodontic treatment involves movement of malpositioned teeth to orthodontically correct locations. During treatment, tiny appliances known as brackets are often fixed to the patient's teeth, and an arch wire is placed in a slot of each bracket. The arch wire forms a track to guide movement of the teeth to desired locations. Ends of the arch wire are often connected to buccal tubes that are in turn secured to the patient's molar teeth. The brackets, buccal tubes and arch wires are commonly referred to as "braces".

Orthodontic brackets are often bonded directly to the patient's teeth by an adhesive. In one technique, a small quantity of adhesive is placed or "buttered" on the base of each bracket and the bracket is then placed on a selected tooth. Next, the bracket is shifted slightly on the tooth as may be needed to bring the bracket to a desired location on the tooth. Once the adhesive has hardened, the bracket is bonded to the tooth with sufficient strength to withstand subsequent forces as orthodontic treatment progresses.

Many practitioners use adhesives known as chemical curing adhesives in the direct bonding technique described above. Chemical curing adhesives are often supplied in two initially separate components that, once mixed together, react and harden to adhere the bracket to the tooth. Typically, the components are mixed together and a small quantity of the mixture is placed on the back of the bracket prior to placing the bracket on the tooth.

However, the direct bonding method as described above when carried out using a chemical curing adhesive is often considered unsatisfactory because the adhesive may unduly harden before the practitioner has had an opportunity to shift the bracket to its precise, intended location on the patient's tooth. For example, if the procedure is interrupted after the components are mixed together, the adhesive may become too stiff to permit the bracket to be shifted across the surface of the tooth. Such an occurrence is preferably avoided, since the ultimate position of the tooth in the oral cavity as treatment progresses is determined to a significant extent by the precise location of the bracket on the tooth. Moreover, the practitioner must take care not to disturb the bracket during the time the adhesive hardens, which may be on the order of 1.5 minutes.

The development of light-curable adhesives for orthodontic treatment has provided many advantages when used in the direct bonding technique described above. Light-curable adhesives include a photoinitiator that initiates the curing reaction once the adhesive is exposed to a sufficient amount of light. Moreover, light-curable adhesives are premixed by the manufacturer and need not be mixed in the orthodontist's office before use.

A common method of using light-curable adhesives for direct bonding includes the steps of placing a small quantity of the adhesive on the base of the bracket and then placing the bracket on the patient's tooth. The practitioner then shifts the bracket on the tooth as may be needed to move the bracket to its intended location. Once the bracket is in its precise, intended location, light from a dental curing unit is directed toward the adhesive for a time period sufficient to satisfactorily cure the adhesive. As can be appreciated, light-curable adhesives are an advantage in that the adhesive does not normally unduly harden until the practitioner has had an opportunity to move the bracket to its intended location and then direct light from the curing unit toward the adhesive.

While the direct bonding techniques described above are in widespread use and are considered satisfactory by many, there are shortcomings that are inherent with such techniques. For example, access to the surfaces of malposed teeth may be difficult. In some instances, and particularly in connection with posterior teeth, the practitioner may have difficulty seeing the precise position of the bracket relative to the tooth surface. Another problem with the above described techniques concerns the significant length of time needed to carry out the procedure of bonding a bracket to each individual tooth, which is a nuisance both to the patient as well as to the practitioner. The risk of moisture contamination from the patient's saliva also increases as the time increases that the patient is occupying the chair. The above factors may also unduly impair the accuracy of placement of the brackets on the teeth and/or increase the chances that the ultimate adhesive bond will not have sufficient strength to retain the brackets on the teeth during the course of orthodontic treatment.

Indirect bonding techniques avoid many of the problems noted above. In general, indirect bonding techniques in the past have involved the use of a transfer tray having a shape that matches the configuration of at least part of one of the patient's dental arches. A set of brackets are releasably connected to the tray at certain, predetermined locations. Once adhesive is applied to the base of each bracket, the tray is placed over the patient's teeth until such time as the adhesive hardens. Next, the tray is detached from the teeth as well as from the brackets, with the result that all of the brackets previously connected to the tray are now bonded to their respective teeth at their intended, predetermined locations.

In more detail, one method of indirect bonding includes the steps of taking an impression of each of the patient's dental arches and then making a replica plaster or "stone" model from each impression. A sealing solution (such as Liquid Foil brand sealing solution, from 3M) is applied to the stone model and allowed to dry. If desired, the teeth of the model can be marked with a pencil to assist in placing the brackets in ideal positions.

Next, the brackets are bonded to the sealed stone models. Optionally, the bonding adhesive can be a chemical curing adhesive (such as Concise brand adhesive from 3M) or a light-curable adhesive (such as Transbond XT or Transbond LR adhesive, from 3M). Optionally, the brackets may be adhesive precoated brackets such as described in U.S. Pat. Nos. 5,015,180, 5,172,809, 5,354,199 and 5,429,299.

A transfer tray is then made by placing matrix material over the model as well as over the brackets on the model. For example, a plastic sheet matrix material may be placed over the model and brackets and then heated in an oven under vacuum. As the plastic sheet material softens and as air in the oven is evacuated, the plastic sheet material assumes a configuration that precisely matches the shape of the replica teeth of the stone model and adjacent brackets.

The plastic material is then allowed to cool and harden to form a tray. The tray and the brackets (which are embedded in an interior wall of the tray) are then detached from the stone model and sides of the tray are trimmed as may be desired. Once the patient has returned to the office, a quantity of adhesive is placed on the base of each bracket and the tray with the embedded brackets is then placed over matching portions of the patient's dental arches. Since the configuration of the interior channel in the tray closely matches the respective portions of the patient's dental arches, each bracket is ultimately positioned on the patient's teeth at precisely the same location that corresponds to the previous location of the same bracket on the stone model.

Both light-curable adhesives and chemical curing adhesives have been used in indirect bonding techniques to secure the brackets to the patient's teeth. If a light-curable adhesive is used, the tray is preferably transparent or translucent. If a two-component chemical curing adhesive is used, the components can be mixed before application to the brackets, or one component may be placed on each bracket base and the other component may be placed on the tooth surface. In either case, placement of the tray with the embedded brackets on corresponding portions of the patient's dental arches enables the brackets to be bonded to the teeth as a group using only a relatively short amount of time that the patient is occupying the chair in the operatory. With such a technique, individual placement and positioning of each bracket in seriation fashion on the teeth is avoided.

While it is apparent that the use of indirect bonding techniques can greatly facilitate precise placement of brackets on the patient's teeth and shorten the amount of time that the patient is in the operatory, there is a need in the art to improve current indirect bonding techniques in order to optimize use of the practitioner's time. For example, conventional techniques using commercially available chemical curing orthodontic adhesives are somewhat time consuming in that the practitioner is often required to firmly press the transfer tray with the embedded brackets against the patient's teeth for at least two minutes and then wait an additional five minutes before removing the tray from the mouth to ensure that the adhesive has cured to a degree sufficient to hold the brackets firmly on the tooth as the tray is released from the brackets and the teeth. Some conventional light-curable adhesives cure somewhat sooner, but require the use of a dental light curing unit and the use of subsequent disinfection and/or sterilization procedures before using the light curing unit with another patient.

SUMMARY OF THE INVENTION

The present invention relates in one aspect to a method of bonding an orthodontic appliance to a tooth that comprises the steps of creating a replica of a patient's tooth structure and releasably fixing at least one orthodontic appliance on the replica. The method also includes the steps of making a transfer tray by placing matrix material over the replica as well as over each appliance, and detaching the transfer tray with each appliance from the replica. The method further includes the steps of placing a first component of an adhesive on a base structure of each appliance, placing a second component of the adhesive on the patient's tooth structure, and placing the transfer tray over the tooth structure such that the first component and the second component contact each other and react to provide a bond for securing the appliance to a tooth structure. The adhesive has a set time of no greater than 60 seconds and the numeric average of the viscosity of the first component at 25° C. and the viscosity of the component at 25° C. is greater than 30 poise using a shear rate of 10 sec$^{-1}$.

Another aspect of the present invention is directed toward a method of indirect bonding for orthodontic treatment that includes the step of providing a transfer tray and at least one orthodontic appliance connected to the transfer tray. The method also includes the steps of placing a first component of an adhesive on base structure of each orthodontic appliance and placing a second component of the adhesive on each of the patient's teeth that is to receive a respective appliance. The method further includes the step of placing the transfer tray with each appliance over the respective teeth such that the first component and the second component contact each other and react to provide a bond for securing each appliance to the respective tooth. The adhesive has a set time of no greater than 60 seconds and the viscosity of the first component at 25° C. and the viscosity of the second component at 25° C. is each greater than 20 poise using a shear rate of 10 sec$^{-1}$.

The present invention is also related to an orthodontic adhesive for use with a transfer tray in an indirect bonding procedure. The adhesive comprises a first component and a second component initially separate from the first component. The adhesive has sufficient strength to secure an orthodontic bracket to a tooth and enable the bracket to be released from a transfer tray within two minutes of the time that the first component and the second component contact each other. The adhesive has a set time of no greater than 60 seconds and the numeric average of the viscosity of the first component at 25° C. and the viscosity of the component at 25° C. is greater than 30 poise using a shear rate of 10 sec$^{-1}$.

The methods and adhesive of the present invention are advantageous in that the relatively fast curing time reduces the length of time that the tray must be firmly held against the patient's teeth as well as the length of time that the tray need remain in the oral cavity before detachment from the teeth and the brackets. The two-component adhesive enables the initially separate components to be precisely placed on both the base structure of the brackets and the selected areas of the patient's tooth surfaces at the practitioner's convenience, and hardening of the adhesive does not begin to occur until such time as the tray is placed over the patient's teeth and the first and second components contact each other. Use of a two-component adhesive also avoids the necessity for chair-side use of a dental light curing unit and the associated time and expense that might otherwise be necessary for disinfection or maintenance of the unit.

Further details of the invention are described in the paragraphs that follow and are illustrated in the accompanying drawings.

DETAILED DESCRIPTION OF THE PREFERRED EMBODIMENTS

In accordance with the indirect bonding method of the present invention according to one embodiment, an impression of one or both of the orthodontic patient's dental arches is taken, using care to avoid undue distortion. Preferably, an alginate impression material is used such as Unijel II brand alginate impression material from 3M Unitek. Alternatively, a hydrocolloid or a vinyl polysiloxane impression material may also be used, such as Imprint brand vinyl polysiloxane impression material from 3M.

A model is then made from each impression. Preferably, the model is made from plaster of Paris, using care to avoid bubbles in the model. If small voids are present, the voids can be filled with a small, additional quantity of plaster of Paris.

Figure 1:
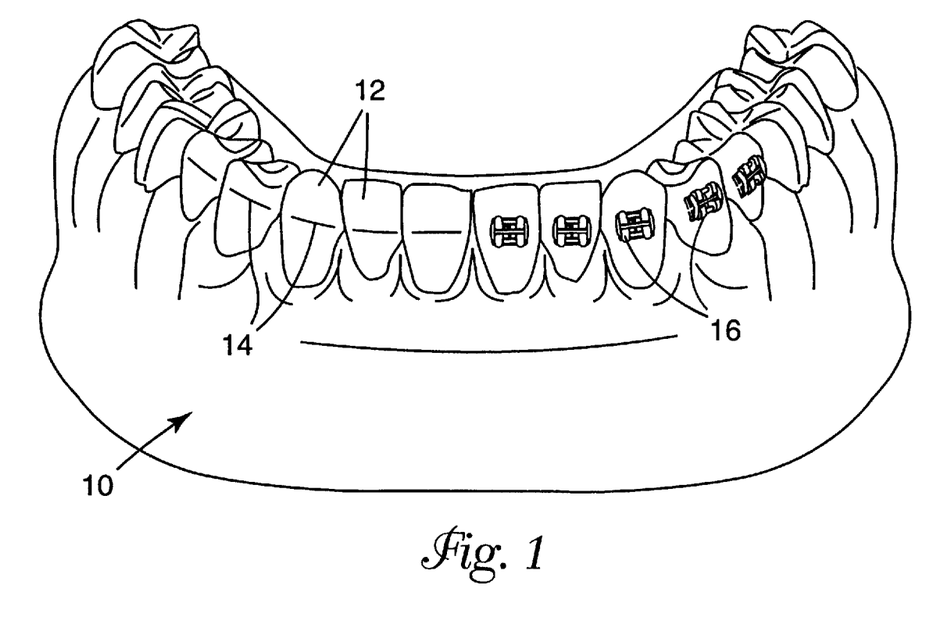
FIG. 1 is a top and front side view showing a model of one dental arch of an orthodontic patient, wherein orthodontic brackets have been placed on some of the teeth of the model to illustrate part of the method of the present invention.

An exemplary plaster of Paris or "stone" model 10 is illustrated in FIG. 1. The model 10 includes a number of replica teeth 12 as well as adjacent portions of the patient's soft tissue 13 or "gums". If the impression is accurately taken and the stone model 10 is carefully prepared, the replica teeth 12 and adjacent portions of the replica soft tissue 13 will have a configuration and orientation that is identical to the configuration and orientation of the corresponding teeth and tissue of the orthodontic patient.

Next, a thin layer of separating medium is applied to the stone model 10 and allowed to dry. Examples of suitable materials are Liquid Foil brand sealing solution from 3M or Al-Cote brand separating medium from Dentsply (which when used is allowed to dry for approximately one hour).

A pencil mark is then made across the labial surface of each replica tooth 12 to assist in subsequent placement of orthodontic brackets. The pencil mark is preferably made with the assistance of a height gauge such as a Boone bracket positioning gauge from 3M Unitek (catalog no. 807-002). The pencil line is drawn across the labial surface of each tooth 12 to serve as a location guide for placement of the arch wire slot of each orthodontic appliance (such as an orthodontic bracket).

For example, for the patient's maxillary or upper dental arch, a pencil mark is drawn parallel to the occlusal plane of the patient at a distance of 4.0 mm from the occlusal edge of the replica central teeth 12 and replica lateral teeth 12. Similar lines are drawn at a distance of 4.5 mm from the occlusal edge of the replica upper cuspid teeth 12 and the replica upper bicuspid teeth 12. On the stone model 10 representing the patient's lower dental arch, pencil lines are drawn parallel to the occlusal plane at a distance of 3.5 mm from the occlusal edge of the replica anterior teeth 12. Similar lines are drawn at a distance of 4.0 mm from the occlusal edge of the replica lower cuspid teeth 12 and replica lower bicuspid teeth 12. On both the upper and lower stone models 10, lines are drawn parallel to the occlusal plane at a distance of 3.5 mm from the occlusal edge of each replica molar tooth (unless the corresponding tooth of the patient will receive a band or will not receive a bracket). In FIG. 1, some of the pencil lines as described above are designated by the numeral 14.

Next, orthodontic appliances such as brackets 16 as selected by the orthodontist are placed on corresponding replica teeth 12 in positions such that the archwire slot of each bracket is approximately aligned with the respective pencil line 14. Before each bracket 16 is placed on the respective replica tooth 12, a quantity of adhesive is coated across the base of the bracket 16.

Preferably, the brackets 16 are adhesive precoated brackets that have a coating of light-curable adhesive applied by the manufacturer to the base of each bracket. Such adhesive precoated brackets are described in U.S. Pat. Nos. 5,015,180, 5,172,809, 5,354,199, and 5,429,299, all of which are assigned to the assignee of the present invention. The brackets 16 may be made of any suitable material such as metal (e.g., stainless steel), ceramic (e.g., translucent polycrystalline alumina) or plastic (e.g., translucent poly carbonate).

If the brackets 16 are not precoated with adhesive by the manufacturer, a coating of adhesive is applied by the practitioner to the base of each bracket. Suitable adhesives include light-curable adhesives such as Transbond XT or Transbond LR adhesives from 3M Unitek. As another option, chemical curing adhesives may also be used, such as Concise brand adhesive from 3M.

Once the brackets 16 have been placed on the replica teeth 12, the brackets 16 are shifted mesio-distally as needed to align the central occlusal-gingival axis of the bracket with the long axis of the tooth. The brackets 16 are also shifted occluso-gingivally as needed to place the archwire slot of each bracket directly over the underlying pencil line 14. Optionally, a gauge such as the Boone bracket positioning gauge mentioned above is used to precisely position the arch wire slot of each bracket 16 the distance specified above from the occlusal edge of the corresponding replica stone tooth 12. Next, the practitioner applies firm pressure to each bracket 16, preferably by using a spatula to apply pressure to the arch wire slot of the bracket 16 to ensure that the bracket 16 is firmly seated on the underlying replica tooth 12. A tool such as a dental explorer is then used to remove any adhesive flash that may have extruded near the periphery of the bracket base.

Figure 2:
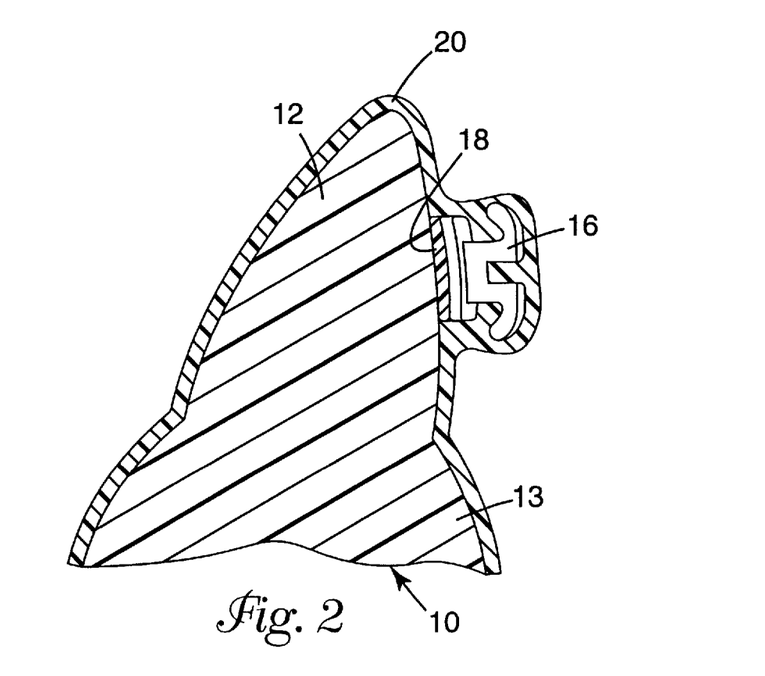
FIG. 2 is an enlarged side cross-sectional view of one of the replica teeth illustrated in FIG. 1 and additionally showing a matrix material that has been formed over the replica tooth and its corresponding bracket.

The adhesive is designated by the numeral 18 in FIG. 2 and is not necessarily drawn to scale. The use of a light-curable adhesive 18 is advantageous since an orthodontist's assistant or lab technician can carry out the steps described immediately above and then give the stone model 10 to the orthodontist. The orthodontist may make a final check as to the precise placement of each bracket 16 on the corresponding replica tooth 12 before the adhesive 18 has hardened. As one example, a number of stone models 10 may be prepared by the assistant or technician and stored in an opaque container such as a black plastic box until reviewed by the orthodontist. In this manner, the orthodontist can review the placement of brackets 16 on a number of different stone models 10 at a convenient time without undue curing of the adhesive 18.

Once the accuracy of the bracket position has been confirmed by the orthodontist, the adhesive 18 is allowed to harden. If a light-curable adhesive 18 is used, the model 10 may be placed in a curing container such as Triad 2000 visible light curing system from Dentsply. Preferably, the curing container is sufficiently large to contain a number of models so that the adhesive on a number of models can be cured simultaneously. In such a container, the light source and the models preferably move relative to each other during energization of the light source to facilitate complete curing of each portion of adhesive.

If the brackets 16 are made of metal or another opaque material and if a light-curable adhesive is used, it is preferable to expose the stone model 10 to the curing light for a relatively long amount of time such as three to five minutes to ensure that the adhesive 18 has sufficiently hardened. As an alternative to the light curing containers mentioned above, a hand-held light curing unit may be used such as Ortholux XT brand curing unit from 3M Unitek.

Next, a transfer tray is made by placing a sheet of matrix material 20 over the stone model 10. A suitable matrix material is Bioplast brand clear plastic sheet (from Scheu-Dental) having a thickness of 1.5 mm and a length and width of 12.5 cm. Alternatively, the matrix material may comprise two or more layers, such as a 1 mm thick layer of Bioplast brand clear plastic sheet material that is covered with a 1 mm thick layer of Biocryl brand clear plastic sheet material. Advantageously, the outer layer is more rigid than the inner layer and provides rigidity to the bonding tray, while the flexible inner layer facilitates removal of the tray from the model 10 as well as subsequent removal of the tray from the oral cavity.

The stone model 10 with the brackets 16 and the matrix material 20 is then placed in a pressurizable oven such as Biostar brand oven. The oven is heated to a temperature suitable to soften the matrix material 20 and is pressurized to ensure close fitting engagement of the softened matrix material 20 with the stone model 10 and the brackets 16. As an example, the oven may be heated to a temperature of 427° F. (220° C.) for 50 seconds at 1.2 bar pressure. The oven is then turned off and the air pressure relieved to allow the stone model 10 and the matrix material 20 to cool.

FIG. 2 shown the configuration of a portion of the matrix material 20 once it has softened and deformed to tightly engage underlying regions of the stone model 10 including the replica teeth 12 and adjacent replica soft tissue 13 as well as the brackets 16. After the stone model 10 has cooled, the stone model 10 is immersed in a bath of water. The plaster absorbs the water and facilitates separation of the matrix material 20 as well as the adhesive 18 from the stone model 10. If necessary, a dental tool can be used to facilitate disengagement of the adhesive 18 from the replica teeth 12 as the matrix material 20 is lifted from the stone model 10. It is important that the hardened adhesive 18 remains affixed to the base of each bracket 16 as the brackets 18 are detached from the replica teeth 12.

Figure 3:
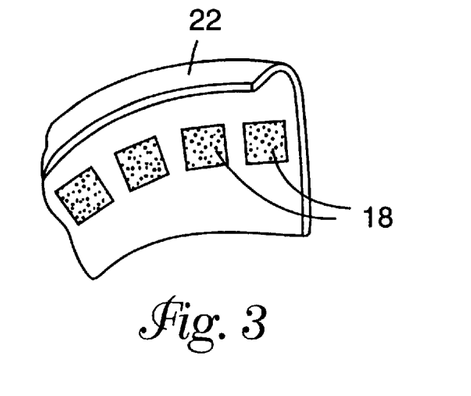
FIG. 3 is a reduced rear perspective view of a transfer tray that has been made from the matrix material shown in FIG. 2 according to the invention, wherein base structure of each of five orthodontic brackets embedded in the transfer tray is in a position for bonding with five respective teeth of the patient.

Once the matrix material 20 and the brackets 16 have been detached from the model 10, the matrix material is trimmed to form a transfer tray 22. As an example, the matrix material 20 may be trimmed across the impression of each tooth that is distal to the tooth receiving the distal-most bracket, and also trimmed gingivally of the gingival margin along the labial and lingual sides of the dental arch impression. Optionally, the tray 22 may be returned to the light curing container for an additional period of curing (such as one minute) to ensure that the adhesive 18 has sufficiently hardened.

Next, any debris that is present (such as small chips from the replica teeth 12) is cleaned from the outer face of the hardened resin 18 using a fluted acrylic bur or other tool. Optionally, the outer face of the adhesive 18 may be cleaned of debris by lightly using a sandblaster. The sandblaster can also serve to roughen and/or pit the outer face of the adhesive to enhance subsequent bonding. Since the adhesive 18 on the base of each bracket 16 now has an outer contour that matches the contour of the corresponding replica tooth 12, the hardened adhesive 18 has formed a custom bracket base structure that closely corresponds to the contour of the matching location of the patient's respective tooth.

The transfer tray 22 with the brackets 16 and the adhesive 18 is then rinsed and/or immersed in an ultrasonic cleaning bath. As an example, the transfer tray 22 along with the brackets 16 and the adhesive 18 may be placed in an ultrasonic cleaning bath for 10 minutes in a solution of dish detergent, and then for 10 minutes in water. The tray 22, the brackets 16 and the adhesive 18 are then allowed to dry.

Preferably, but not necessarily, the transfer tray 22 is subsequently cut into sections to facilitate handling and subsequent bonding. For example, the tray 22 may be cut into a section that matches one quadrant of the patient's arches as shown in FIG. 3. Smaller sections may also be made if desired. The tray 22 has a curved central longitudinal axis that matches the shape of the corresponding arch or portion of the arch.

Figure 4:
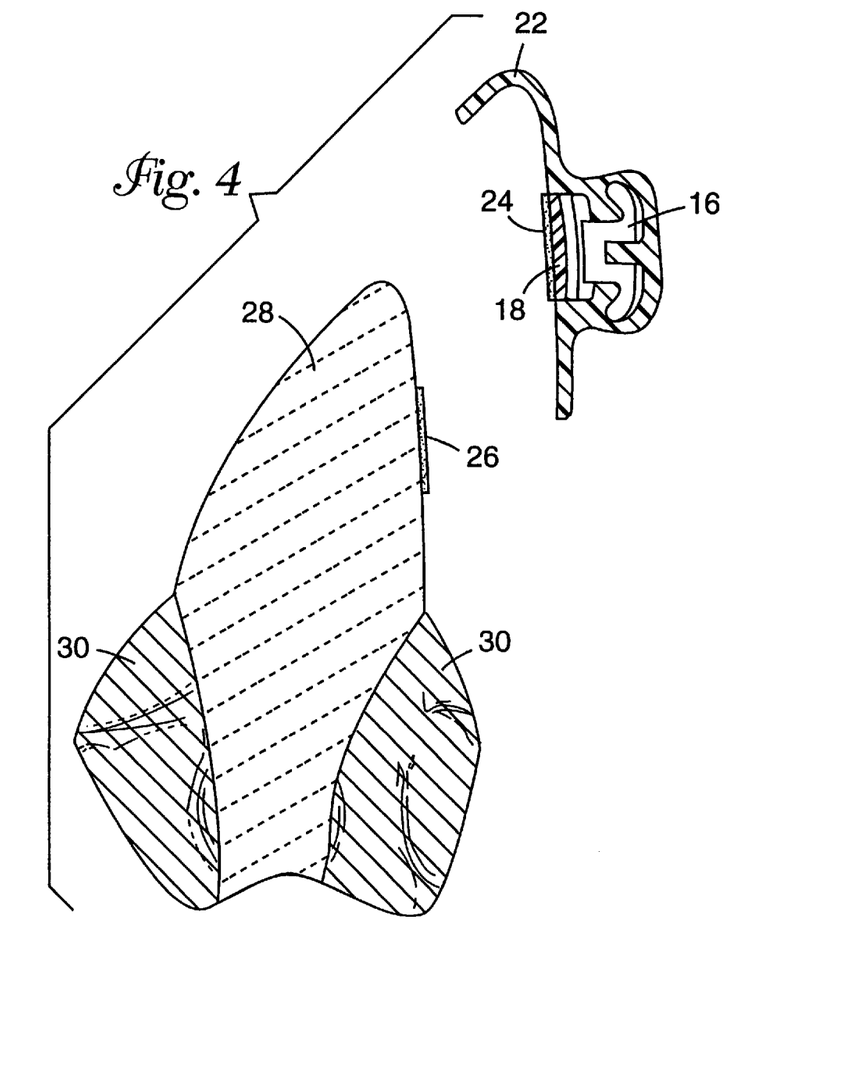
FIG. 4 is an enlarged side cross-sectional view of the transfer tray illustrated in FIG. 3 and also showing one of the patient's teeth that is about to receive the tray and one of the brackets embedded in the tray.

Next, the transfer tray 22 is trimmed further. As an example, and as shown in FIGS. 3 and 4, the tray 22 may be trimmed on its lingual side along a line that corresponds to a location approximately three-quarters of the distance from the lingual side of the gingival edge to the occlusal edge of the teeth. The labial side of the tray 22 is also trimmed along a line that corresponds to a location next to and along the occlusal side of the gingival margin. The trimmed tray 22 preferably has a curved, somewhat "J"-shaped configuration in inverted cross-sectional view as depicted in FIG. 3.

Once the patient has returned to the office, the patient's teeth that are to be bonded are isolated using cheek retractors, tongue guards, cotton rolls, dry angles and/or other articles as needed. The teeth are then thoroughly dried using pressurized air from an air syringe. Etching solution (such as 3M Unitek Transbond XT etching gel) is then dabbed onto the teeth in the general area that is to be covered by the brackets, taking care to prevent the etching solution from flowing into interproximal contacts or engaging the skin or gingiva.

After the etching solution has remained on the selected tooth surfaces for a period of approximately 30 seconds, the solution is rinsed away from the teeth with a stream of water for 15 seconds. The teeth are then dried by application of pressurized air from the air syringe for 30 seconds, and excess water is removed by suction. Care should be undertaken to ensure that saliva does not come into contact with the etched enamel surfaces. The cotton rolls and other absorbent devices are replaced, again making sure that saliva does not contact the etched enamel. Air from the air syringe is then applied to the teeth again to ensure that the teeth are thoroughly dry.

Next, a bonding adhesive is applied to the hardened adhesive 18 and/or the selected areas of the patient's teeth. Preferably, the adhesive is a two-component adhesive. The first component (designated by the numeral 24 in FIG. 4) is applied to the hardened adhesive 18 and the second component (designated by the numeral 26 in FIG. 4) is applied to the area of the patient's tooth 28 that is to receive the bracket 16. For purposes of illustration, the components 24, 26 are not drawn to scale in FIG. 4.

After the first component 24 has been applied to the hardened adhesive 18 of each bracket 16 and after the second component 26 has been applied to each corresponding area of the patient's tooth structure, the tray 22 is then positioned over the corresponding teeth 28 and seated with a swinging, hinge-type motion. Since the interior shape of the tray 22 matches the shape of the underlying teeth 28 and gingival portions 30, the brackets 16 are simultaneously seated against the underlying teeth 28 at precisely the same locations corresponding to the previous position of the brackets 16 on the stone model 10. Equal pressure is applied with the fingers to the occlusal, labial and buccal surfaces of the transfer tray 22. Firm pressure is applied to the tray 22 until such time as the bonding adhesive has sufficiently hardened.

Subsequently, the tray 22 is carefully removed from the patient's dental arch. A preferred removal method involves gently peeling the tray 22 from the lingual side to the buccal side, and carefully removing the tray as needed around the tiewings of the brackets 16. The flexibility of the tray 22 allows portions of the tray 22 to deform and spread apart in regions near the brackets 16, especially during tray removal, an important aspect in regions where tiewings of the brackets 16 present projections, undercut areas or recesses. Any excess bonding adhesive resulting from the components 24, 26 is then removed from areas next to the edges of the bracket bases and/or the adjacent tooth surfaces.

The chemically curable bonding adhesive comprises two initially separate components that, when mixed together, initiate a cure reaction that will result in polymerization of the adhesive and bonding of the orthodontic appliances to teeth. This cure reaction takes place without the need to expose the chemically curable bonding adhesive to actinic light. Optionally, the chemically curable dental adhesive may be provided in a three or more component formulation. Upon mixing, the components react, initiating a polymerization reaction.

A preferred mode for initiation of the polymerization reaction of an ethylenically unsaturated moiety is the incorporation of an oxidizing agent and a reducing agent as a redox catalyst system to enable the bonding adhesive to cure via a redox reaction. Various redox systems are described in U.S. Pat. No. 5,154,762, the disclosure of which is expressly incorporated herein by reference.

The oxidizing agent should react with or otherwise cooperate with the reducing agent to produce free radicals capable of initiating polymerization of the ethylenically unsaturated moiety. The oxidizing agent and the reducing agent preferably are sufficiently shelf stable to permit their storage and use under typical dental conditions. The oxidizing agent and the reducing agent should also be present in an amount sufficient to permit an adequate free radical reaction rate. This can be evaluated by combining the ethylenically unsaturated moiety, the oxidizing agent and the reducing agent and observing whether or not a hardened mass is obtained.

Suitable oxidizing agents include persulfates such as sodium, potassium, ammonium and alkyl ammonium persulfates, benzoyl peroxide, hydroperoxides such as cumene hydroperoxide, tert-butyl hydroperoxide, tert-amyl hydroperoxide and 2,5-dihydroperoxy-2,5-dimethylhexane, salts of cobalt (III) and iron (III), hydroxylamine, perboric acid and its salts, salts of a permanganate anion, and combinations thereof. Hydrogen peroxide can also be used, although it may, in some instances, interfere with the photoinitiator, if one is present. The oxidizing agent may optionally be provided in an encapsulated form as described in U.S. Pat. No. 5,154,762.

Preferred reducing agents include ascorbic acid, metal complexed ascorbic acid, cobalt (II) chloride, ferrous chloride, ferrous sulfate, hydrazine, hydroxylamine, oxalic acid, thiourea, tertiary aromatic amines (such as N,N-bis-(2-hydroxyethyl)-p-toluidine ("DHEPT"), 4-(dimethylamino)-phenethyl alcohol and the like), and aromatic salts of a dithionite, thiosulfate, benzenesulfinate, or sulfite anion.

A preferred bonding adhesive is obtained by combining (1) Bis-GMA with (2) a hydrophilic monomer such as hydroxyethyl methacrylate, hydroxypropyl methacrylate, or methacrylic acid. Suitable monomers for use in the bonding adhesive include the monomers described above as well as tetrahydrofurfuryl methacrylate, glyceryl-1,3-dimethacrylate, triethyleneglycol dimethacrylate, ethyl methacrylate, n-hexyl methacrylate, polyethyleneglycol dimethacrylate, and 1,6-hexanediol dimethacrylate. Other suitable free-radically polymerizable compounds include mono- or poly- (e.g., di-, tri- or tetra-functional) acrylates and methacrylates such as methyl acrylate, 2-hydroxyethyl acrylate, triethyleneglycol diacrylate, neopentylglycol diacrylate, hexamethyleneglycol diacrylate, trimethylolpropane triacrylate, pentaerythritol tetraacrylate, polyalkylene glycol mono- and di-acrylates, urethane mono- or polyfunctional acrylates, Bisphenol A diacrylates, and the corresponding methacrylates of the above compounds, as well as acrylamides and methacrylamides, vinyl compounds, styrene compounds, and other olefinically unsaturated compounds suitable for use in the oral environment. U.S. Pat. Nos. 4,499,251, 4,515,930, 4,537,940 and 4,539,382 contain an extensive list of such compounds. Optionally, the bonding adhesive may contain polymers. The bonding adhesive can also contain cosolvents of the type described above. If desired, the bonding adhesive can contain conventional fillers, and can also contain adjuvants such as viscosifiers, dilvents, medicaments, preservatives, colorants and the like.

Other preferred bonding adhesives which can be employed with the present invention contain acrylate- or methacrylate-functional polymers and may also contain phosphorous compounds. In such bonding adhesives either a single phosphorus compound or a mixture of phosphorus compounds can be used.

The compound 24 preferably includes at least 3% by weight of benzoylperoxide ("BPO") and the component 26 preferably includes at least 3% by weight of DHEPT. The percentage by weight of BPO and DHEPT in the components 24, 26 respectively preferably adds to a total of at least 4 percent and more preferably adds to a total of at least 5 percent. Such parameters provide sufficiently short working and setting times to carry out the relatively quick bonding procedure set out above.

Preferably, one or both of the components contain a filler. Fillers may be selected from one or more of any material suitable for incorporation in compositions used for medical applications, such as fillers currently used in dental restorative compositions and the like. The filler is finely divided and preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or non-radiopaque.

Examples of suitable inorganic fillers are naturally-occurring or synthetic materials, including glasses and crystalline material, such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169. Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glasses have the added benefit of releasing fluoride at the site of dental work when placed in the oral environment.

Optionally, the surface of the filler particles may be treated with a surface treatment such as a coupling agent in order to enhance the bond between the filler and the polymerizable resin. The coupling agent may be functionalized with reactive curing groups, such as acrylates, methacrylates, epoxies, and the like. An example of a suitable coupling agent is silane.

Preferably, the components combined contain a total of 4.5 percent by weight of filler. A suitable filler is fumed silica. The filler not only helps to avoid bracket drift (when the tray 22 is not used) but also advantageously helps to fill microvoids where present.

The components 24, 26 when mixed together by placement of the bracket 16 on the surface of each tooth 28 harden in a relatively short amount of time so that the tray 22 can be immediately removed from the patient's oral cavity even though the brackets 16 are embedded in the tray 22. Preferably, the bond between the bracket 16 and the tooth surface resulting from contact of the component 24 with the component 26 has sufficient strength within two minutes of the time that the first component 24 contacts the second component 26 to enable removal of the tray 22 from the tooth and then from the oral cavity without significantly changing the position of the bracket 16 on the tooth. More preferably, such bond has sufficient strength within 1.5 minutes of the time that the component 24 contacts the component 26 to enable removal of the tray 22 from the tooth 28 without significantly changing the position of the bracket 16 on the tooth 28. As can be appreciated, the bond must have sufficient strength to firmly retain the brackets 16 on the teeth even though the tray 22 must be pulled with sufficient force to deform the tray 22 in areas near the brackets 16 during tray removal.

Preferably, the bond resulting from components 24, 26 provides a bond strength for retaining a bracket on a tooth of at least 10 lb. (4.5 kg) and more preferably at least 12 lb. (5.4 kg) after a time period of 24 hours has elapsed from the time of initial contact of the component 24 with the component 26. Also, the bond resulting from the components 24, 26 preferably provides a bond strength for retaining a bracket on a patient's tooth of at least 4 lb. (1.8 kg) and more preferably at least 7 lb. (3.2 kg) after a time period of two minutes has elapsed from the time of initial contact of the component 24 with the component 26. More preferably, the bond resulting from the components 24, 26 provides a bond strength for retaining a bracket on a patient's tooth of at least 7 lbs. (3.2 kg) after a time period of one minute has elapsed from the time of initial contact of the component 24 with the component 26. The bond strengths are determined using an Instron brand universal testing machine with a cross-head speed of 0.5 in./min. (1.2 cm./min), and by connecting wire loops to both occlusal and gingival tiewings of the bracket affixed to a bovine tooth to obtain a tensile debonding value.

The relatively fast-setting bonding adhesive of the present invention is an advantage in that the tray 22 can be immediately removed from the patient's oral cavity and the practitioner may attend to other tasks or procedures without undue delay. Moreover, by removal of the tray 22 from the patient's oral cavity immediately after the brackets 16 are bonded to the patient's teeth 28, the tray 22 does not obstruct the practitioner's view or hinder movement of another tray into the patient's oral cavity in order to bond brackets to the patient's remaining teeth. The relatively fast-setting bonding adhesive also enables the practitioner to insert an archwire in slots of the brackets 16 as soon as all of the brackets 16 of interest have been bonded to respective teeth 28 and the trays have been detached.

The adhesive has a set time of no greater than 60 seconds, and preferably has a set time of no greater than 30 seconds. The set time is determined by placing an equal quantity of the first component and the second component in a mixing well and then stirring the components for 10 seconds; the set time is the time that has elapsed from the time that the first and second components initially contact each other to the time when the mixed components suddenly solidify.

The viscosity of the components 24, 26 before the bonding adhesive has hardened is an important aspect of the present invention. The viscosity should be sufficiently high so that any pits or recesses in the hardened adhesive are filled and remain filled by the components 24, 26 as the latter harden. A sufficiently high viscosity also helps to ensure that the bonding adhesive once hardened fills substantially all of the space between the hardened adhesive 18 and the surface of the tooth. However, the viscosity of the components 24, 26 should also be sufficiently low to ensure good mixing of the components 24, 26 as the bracket 16 is pressed against the surface of the tooth 28. Preferably, the viscosities of the components 24, 26 are somewhat similar to promote such mixing.

Preferably, the numeric average of the viscosity of the first component at 25° C. and the viscosity of the second component at 25° C. (i.e., one-half of the sum of both viscosities) is greater than 30 poise using a shear rate of 10 $\sec^{-1}$. Additionally, the visocsity of the first component at 25° C. and the viscosity of the second component at 25° C. is each greater than 20 poise using a shear rate of 10 $\sec^{-1}$. A suitable rheometer for determining viscosities is a parallel plate rheometer such as "RDA-2" brand controlled strain rheometer from Rheometrics Scientific, with plate diameter of 25 mm and a gap of 1 mm; the viscosity is determined at 25° C. with a shear rate of 10 $\sec^{-1}$.

EXAMPLE 1

A bonding adhesive was made of two liquid components. The first component (corresponding to the first component 24) included 61.7% by weight of diglycidylmethacrylate of Bisphenol A ("Bis-GMA") and triethyleneglycol dimethacrylate ("TEGDMA") wherein the weight ratio of Bis-GMA to TEGDMA was 90:10. The mixture of the first component also included an additional 33.22% by weight of TEGDMA, 5.0% by weight of benzoylperoxide ("BPO") and 0.08% by weight of butylated hydroxytoluene ("BHT"). The second component (corresponding to the second component 26) included 61.75% by weight of the 90:10 Bis- GMA/TEGDMA mixture described above, 33.25% by weight of TEGDMA and 5.0% by weight of n,n-bis-(2-hydroxyethyl)-p-toluidine ("DHEPT").

EXAMPLE 2

Work and set times were measured for the adhesive described in Example 1 by adding 4 drops of the second component to a plastic cup having a diameter of 10 mm and a height of 7 mm. Four drops of the first component were then added and the timer was immediately started. The first component and the second component were mixed for 10 seconds with a glass mixing rod. The working time was determined by slowly lifting a small portion of the mixed components with a dental explorer. The work time was determined when the lifted quantity mixed components sagged to form a string-like configuration having a length of at least 1 cm. The set time was determined by visual inspection and was reached when the entire mass of the mixed components suddenly solidified. The test was carried out at room temperature (27° C.). The work time included the 10 seconds of mixing time, and the set time included the work time.

The mixture described in Example 1 was determined to have a work time of 15 seconds and a set time of 20 seconds. The set time of 20 seconds is sufficiently small to avoid undue delay of the procedure and enables the practitioner to remove the transfer tray from the patient's oral cavity in a relatively short amount of time. As a result, the time used by the practitioner for carrying out the procedure and the time that the patient occupies the dental chair are significantly reduced in comparison to conventional procedures.

EXAMPLE 3

The strength of metal orthodontic brackets bonded to bovine teeth was determined using the bonding adhesive described in Example 1. A quantity of light curable adhesive (Transbond XT adhesive, from 3M Unitek Corporation) was applied to the base of metal orthodontic brackets (miniature twin lateral brackets, catalog no. 017-333, from 3M Unitek). The brackets were bonded to plaster of Paris models of the bovine teeth which had been previously sealed with Liquid Foil brand scaling solution. The adhesive was cured by directing light from a light curing unit Triad 2000, from Dentsply for 2 minutes. The brackets together with the hardened light curable adhesive were removed from the replica teeth, and light was directed from the curing light mentioned above in a direction perpendicularly toward the bracket base for an additional 5 seconds. The hardened light curable adhesive of each bracket was then lightly sandblasted using a Micro-Etcher Brand sandblaster (from Danville Equipment) and using 50 micron aluminum oxide grit. The brackets with the hardened adhesive were subsequently rinsed in tap water to remove traces of grit and then dried in a 60° C. oven for 15 minutes.

Selected bovine teeth were mounted in a cold cure material (acrylic monomer, part no. 703-302 from Walther and polymer, part no. 703-202 from Walther). The teeth were pumiced using a horse hair wheel and a slurry of pumice to remove any organic film or discoloration. The teeth were then thoroughly rinsed in water and blotted dry on a paper towel. A 37% phosphoric acid solution (3M Unitek etchant, catalog no. 704-037) was applied to the teeth for 15 seconds, and the teeth were again rinsed thoroughly under running water to remove any excess acid solution. Care was taken to avoid contact with the etched tooth surface. The teeth were then dried with a warm stream of dry, oil-free air and checked for a chalky, white appearance. If shiny areas were present on the teeth, the etching procedure described above was repeated.

Next, the brackets were bonded to the appropriate corresponding bovine teeth by applying the first component described Example 1 to the hardened light curable adhesive on the bracket base and the second component described in Example 1 to the surface of the bovine teeth. The brackets were firmly pressed against the teeth using finger pressure for a period of approximately 1 second. The bovine teeth with the bonded brackets were then stored overnight in a 37° C. water bath.

The brackets were mounted on the bovine teeth with the labial side facing upwardly. A first wire loop was placed under the occlusal tiewings of each bracket and a second wire loop was placed under the gingival tiewings of each bracket. The wire loops were connected to a clip. The test specimens were mounted in an Instron brand universal testing machine such that the upper jaw of the machine gripped the clip. A crosshead speed of 0.2 in./min. (5.1 mm/min) was used.

Upon debonding, the bracket base was observed to determine the extent of coverage of the two-component bonding adhesive. On each bracket, at least 75% of the bracket base was determined by visual inspection to be covered by the two-component adhesive.

The bond strength of two sets of five brackets mounted on bovine teeth as described above was measured. After one minute from the time that the first component contacted the second component, the mean bond strength of the five brackets of the first set was 7.6 lb (3.4 kg) with a standard deviation of 4.7 lb (2.1 kg). After 24 hours from the time that the first component contacted the second component, the mean bond strength of the five brackets of the second set was 12.9 lb. (5.8 kg) with a standard deviation of 1.2 lb (0.5 kg). Such bond strengths are sufficient to enable the tray to be detached from the brackets without disturbing the position of the brackets, and also to retain the brackets on patient's teeth under normal conditions during typical orthodontic treatment procedures.

Those skilled in the art may recognize that a number of modifications and additions may be made to the embodiments set out above without departing from the spirit or the scope of the invention. As a consequence, the invention should not be deemed limited to the presently preferred embodiments described in detail, but instead only by a fair scope of the claims that follow along with their equivalents.

We claim:

1. A method of indirect bonding an orthodontic appliance to a tooth comprising the steps of:

creating a replica of a patient's tooth structure;

releasably fixing at least one orthodontic appliance on the replica;

making a transfer tray by placing matrix material over the replica as well as over each appliance;

detaching the transfer tray with each appliance from the replica;

placing a first component of an adhesive on base structure of each appliance;

placing a second component of the adhesive on the patient's tooth structure; and placing the transfer tray over the tooth structure such that the first component and the second component contact each other and react to provide a bond for securing each appliance to the tooth structure, wherein the adhesive has a set time of no greater than 60 seconds, and wherein the numeric average of the viscosity of the first component at 25° C. and the viscosity of the second component at 25° C. is greater than 30 poise using a shear rate of 10 sec$^{-1}$.

2. The method of claim 1, wherein the step of creating a replica is carried out by taking an impression of the patient's tooth structure.

3. The method of claim 1, wherein the step of releasably fixing the orthodontic appliance on a replica is carried out using a light-curable adhesive.

4. The method of claim 3, wherein each orthodontic appliance is an adhesive precoated appliance.

5. The method of claim 1, wherein the first component has a viscosity at 25° C. greater than about 20 poise using a shear rate of 10 sec$^{-1}$.

6. The method of claim 1, wherein the second component has a viscosity at 25° C. greater than about 20 poise using a shear rate of 10 sec$^{-1}$.

7. The method of claim 1, wherein the bond has sufficient strength within 1.5 minutes of the time that the first component contacts the second component to enable removal of the tray from the oral cavity without significantly changing the position of the appliance on the tooth structure.

8. The method of claim 1, wherein the bond has sufficient strength within two minutes of the time that the first component contacts the second component to withstand the force of an archwire placed in a slot of the appliance.

9. The method of claim 1, wherein at least one of the first component and the second component contains a filler.

10. A method of indirect bonding for orthodontic treatment that includes the steps of:

providing a transfer tray and at least one orthodontic appliance connected to the transfer tray;

placing a first component of an adhesive on base structure of each orthodontic appliance;

placing a second component of the adhesive on each of the patient's teeth to receive a respective appliance; and placing the transfer tray with each appliance over the respective teeth such that the first component and the second component contact each other and react to provide a bond for securing each appliance to the respective tooth, wherein the adhesive has a set time of no greater than 60 seconds, and wherein the viscosity of the first component at 25° C. and the viscosity of the second component at 25° C. is each greater than 20 poise using a shear rate of 10 sec$^{-1}$.

11. The method of claim 10, wherein the numeric average of the viscosity of the first component at 25° C. and the viscosity of the second component at 25° C. is greater then 30 using a shear rate of 10 sec$^{-1}$.

12. The method of claim 10, wherein the adhesive has a set time of no greater than 30 seconds.

13. The method of claim 10, wherein the bond has sufficient strength within 1.5 minutes of the time that the first component contacts the second component to enable removal of the tray from the tooth without significantly changing the position of the appliance on the tooth.

14. The method of claim 10, wherein the bond has sufficient strength within two minutes of the time that the first component contacts the second component to withstand the force of an archwire placed in a slot of the appliance.

15. The method of claim 10, wherein at least one of the first component and the second component contains a filler.

16. An orthodontic adhesive for use with a transfer tray in an indirect bonding procedure, the adhesive comprising a first component and a second component initially separate from the first component, said adhesive having sufficient strength to secure an orthodontic bracket to a tooth and enable the bracket to be released from a transfer tray within two minutes of the time that the first component and the second component contact each other, wherein the adhesive has a set time of no greater than 60 seconds and the numeric average of the viscosity of the first component at 25° C. and the viscosity of the component at 25° C. is greater than 30 poise using a shear rate of 10 sec$^{-1}$.

17. The orthodontic adhesive of claim 16, wherein the viscosity of the first component at 25° C. and the viscosity of the second component at 25° C. is each greater than 20 poise using a shear rate of 10 sec$^{-1}$.

18. The orthodontic adhesive of claim 16, wherein the adhesive has sufficient strength to secure an orthodontic bracket to a tooth and enable the bracket to be released from a transfer tray within 1.5 minutes of the time that the first component and the second component contact each other.

19. The orthodontic adhesive of claim 16, wherein the adhesive has sufficient strength to secure an orthodontic bracket to a tooth and withstand the force of an archwire placed in a slot of the bracket within two minutes of the time that the first component and the second component contact each other.

20. The orthodontic adhesive of claim 16, wherein at least one of the first component and the second component contains a filler.

* * * * *